US00PP13515P2

(12) United States Plant Patent
Lemon

(10) Patent No.: US PP13,515 P2
(45) Date of Patent: Jan. 28, 2003

(54) GERANIUM PLANT NAMED 'CANDY LIGHT SALMON'

(75) Inventor: David Lemon, County of Santa Barbara, CA (US)

(73) Assignee: Oglevee, Ltd., Connellsville, PA (US)

( * ) Notice: Subject to any disclaimer, the term of this patent is extended or adjusted under 35 U.S.C. 154(b) by 0 days.

(21) Appl. No.: 09/877,265

(22) Filed: Jun. 8, 2001

(51) Int. Cl.[7] ..... A01H 5/00
(52) U.S. Cl. ..... Plt./328
(58) Field of Search ..... Plt./328

*Primary Examiner*—Bruce R. Campell
*Assistant Examiner*—Annette H. Para
(74) *Attorney, Agent, or Firm*—Webb Ziesenheim Logsdon Orkin & Hanson, P.C.

(57) ABSTRACT

A new and distinct zonal geranium plant with coral-salmon colored flowers above dark green foliage.

1 Drawing Sheet

CLASSIFICATION

*Pelargonium×hortorum* (zonal geranium).

VARIETAL DENOMINATION

'Candy Light Salmon'.

BACKGROUND OF THE INVENTION

The present invention comprises a new and distinct cultivar of *Pelargonium×hortorum* known by the varietal name 'Candy Light Salmon', Breeder No. 6DG2606-2. The new variety was discovered in Lompoc, Calif. The new variety is a result of cross breeding of 'Eclipse Light Salmon' (female) (U.S. Plant Pat. No. 7,926) and Seedling Salmon #1279 (male) (unpatented). The new variety exhibits similar plant growth to 'Eclipse Light Salmon' and has deeper colored flowers than both parents. The new variety was first asexually reproduced by cuttings in Lompoc, Calif. The new variety has been trial and field tested and has been found to retain its distinctive characteristics and remain true to type through successive propagations.

The new variety was grown in a glass greenhouse in Connellsville, Pa. using full light, 60° F. night temperature and 68° F. day temperature and grown in a soilless media with constant fertilizer at 200–250 ppm nitrogen and potassium.

DESCRIPTION OF THE DRAWING

The accompanying photographic drawing illustrates the new variety, with the color being as nearly true as is possible with color illustrations of this type.

DESCRIPTION OF THE PLANT

The following detailed description sets forth the characteristics of the new cultivar from a plant at 9 weeks old from a rooted cutting. The data which defines these characteristics were collected by asexual reproductions carried out at Oglevee, Ltd. in Connellsville, Pa. The color readings were taken on Apr. 14, 2000 indoors under 200–220 foot candles of cool white fluorescent light. Color references are primarily to The R.H.S. Colour Chart of The Royal Horticultural Society of London.

PLANT

Form: Medium mound.
Height: 21–23 cm to top of foliage.
Growth: Upright, basal branching.
Strength: Does not require artificial support.
Rooting: 14–21 days to visible root.
Foliage: Stalked leaf arrangement; zone barely noticeable.
Leaves:
- *Size.*—7.0–9.5 cm long; 6.0–8.0 cm wide.
- *Shape.*—Reniform; cordate base.
- *Margin.*—Crenate.
- *Texture.*—Smooth; pubescent.
- *Color.*—Upper surface: Green Group 137A. Lower surface: Green Group 137D.
- *Ribs and veins.*—Type: Palmate. Color: Yellow-Green Group 144C.

Petioles:
- *Color.*—Yellow-Green Group 144A with Greyed-Purple Group 187B.
- *Length.*—7.5–9.0 cm.

Stem/branches:
- *Color.*—Yellow-Green Group 144B.
- *Internode length.*—3.0–3.5 cm.

THE BUD

Shape when just showing color:
- *Overall.*—Round.
- *Individual bud.*—Round, elliptical.

Size when just showing color:
- *Umbel.*—4.0 cm wide.
- *Individual bud.*—5–10 mm wide; 11–13 mm long.

INFLORESCENCE

Blooming habit: Continuous and free; early flowering.
Size of umbel: 9–11 cm.
Borne: Flowers on pedicel; pedicel on peduncle; 8.0–11.0 cm above foliage.
Number of flowers per umbel: 9–15.
Flowers:
- *Form.*—Ruffled; open flat to slightly cupped.
- *Size.*—4.5–5.0 cm wide; 1.0–1.5 cm deep.
- *Petals.*—Shape: Obovate. Size: 1.5–2.1 cm wide; 2.5–3.0 cm long. Margin: Entire. Number per flower: 10–15. Color: Upper surface: Outer edge Red Group 49C shading to a darker Red Group 49A at middle of petal. Red Group 49A continues toward the base of the petal which is white. Some petals are darker having some areas of Red Group 38A and some with minimal areas of Red Group 37A. Darker veining of Red Group 49A is present on the areas of Red Group 49C. Some petals are lighter being white at areas near the outer edge shading to the same darker colors toward the center and the base of the petals. Lower surface: Red Group 49D. Darker veining of Red Group 48A is visible on some petals.

*Texture.*—Highly reflective; smooth; velvety.

*Tonality from a distance.*—Coral-salmon petals with degrees of intensity ranging from white, peach and pale pink to coral and light salmon.

Petaloids:

*Number.*—0–5.

*Shape.*—Irregular; twisted; tubular; cut edges.

*Color.*—Same as petals.

Pedicel:

*Length.*—3.0–3.3 cm.

*Color.*—Greyed-Orange Group 173A, sometimes darker Greyed-Orange Group 174A.

Peduncle:

*Length.*—18–21 cm.

*Color.*—Yellow-Green Group 144A at base to Greyed-Purple Group 187B.

Disease/pest resistance: No unusual susceptibility to diseases or pests has been noted to date.

Lasting quality: Individual flowers and umbels last 7–14 days.

Fragrance: None.

REPRODUCTIVE ORGANS

Stamens:

*Quantity.*—3–8, often attached to petaloids or sterile.

*Anthers.*—2–3 mm long.

*Filaments.*—Length: 5–7 mm. Color: White with coral colored tips.

*Pollen color.*—Orange.

Pistils:

*Number.*—One.

*Length.*—10–11 mm.

*Stigma.*—Number: One. Color: Red Group 48A.

*Style.*—Length: 3 mm. Color: Red Group 48A.

Ovaries:

*Color.*—Green with light burgundy tips.

*Length.*—5–6 mm.

*Width.*—2–3 mm.

*Pubescence.*—Very pubescent.

Fruit: None.

I claim:

1. A new and distinct variety of zonal geranium plant substantially as shown and described.

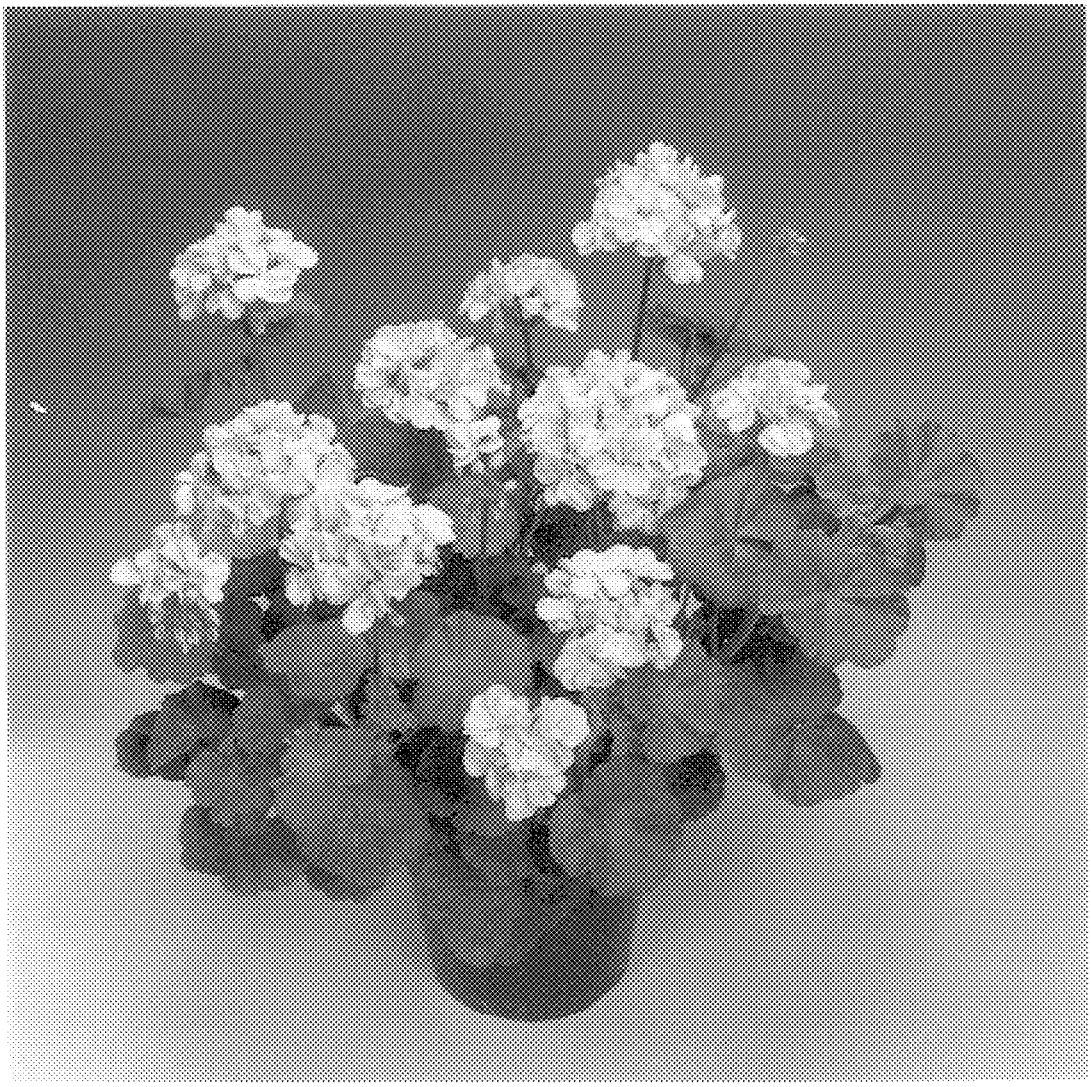

* * * * *